United States Patent [19]

Ivory

[11] Patent Number: 5,071,536
[45] Date of Patent: Dec. 10, 1991

[54] HIGH RESOLUTION CONTINUOUS FLOW ELECTROPHORESIS

[76] Inventor: Cornelius F. Ivory, 1114 Enchanted Forest, South Bend, Ind. 46624

[21] Appl. No.: 801,580

[22] Filed: Nov. 25, 1985

[51] Int. Cl.[5] .................. G01N 27/26; B01D 57/02
[52] U.S. Cl. .......................... 204/299 R; 204/180.1; 204/182.1
[58] Field of Search ............. 204/299 R, 180.1, 182.1

[56] References Cited

U.S. PATENT DOCUMENTS 4,204,929  5/1980  Bier .............................. 204/180 R
4,362,612  12/1982 Bier .............................. 204/301

FOREIGN PATENT DOCUMENTS 1150722  4/1969  United Kingdom .
1186184  4/1970  United Kingdom .

OTHER PUBLICATIONS

Ivory et al., in Electrophoresis '83, H. Hirai ed. Walter de Gruytor & Co., Berlin, 1984.
Hannig, 3 Electrophoresis 235-243 (1982).
Gobie et al., AICHE Abstract, p. T-6, Paper 5b, Nov. 26, 1984.
Gobie et al., ACS Abstract No. 157, (1985).
Gobie et al., 1 Biotechnology Progress 60-68 (1985).

Primary Examiner—John F. Niebling
Assistant Examiner—John S. Starsiak, Jr.

[57] ABSTRACT

Recycle continuous flow electrophoresis (RCFE) makes use of an electrophoresis chamber having a plurality of inlet ports and a plurality of outlet ports disposed opposite the inlet ports. The flow exiting through an outlet port is recycled to an inlet port which is displaced by a distance $\Delta$ from the inlet port directly opposite the outlet port. The distance $\Delta$ is calculated using various physical parameters for the separation system and electrophoretic mobilities of the solutes. Improved resolution and reduced power requirements are achieved using the system. In addition, regeneration sections can be included to eliminate dilution of the separated solutes.

4 Claims, 4 Drawing Sheets

HIGH RESOLUTION CONTINUOUS FLOW ELECTROPHORESIS

The invention which is the subject matter of this application was made under a grant from the National Science Foundation, and the Government has certain rights in the invention.

BACKGROUND OF THE INVENTION

The present invention relates to an apparatus and method for high resolution continuous flow electrophoresis, and makes use of a shifted recycle of the solvent-/solute flow to achieve high resolution without solute dilution.

Electrophoretic separations take advantage of the differential mobility of solute materials in an external electric field. Solutes will migrate in the field at differing rates which are dependent on parameters such as charge, size, and diffusion coefficient of the solute, and ionic strength of the buffer. If the mobilities of the solutes to be separated are only slightly different, a longer duration of exposure to the electric field will be required to achieve separation. This longer time, however, increases the importance of dispersive effects, and leads to a broadening of the solute containing region leading to solute dilution and a loss of resolution.

Gel electrophoresis is one technique which has been employed for separations. In this technique, dispersive effects are minimized by performing the separation in a gel matrix. Regions of the gel containing the separated solute bands can then be excised, and the solutes recovered from the gel. This technique works well on an analytical scale, but it has obvious limitations which detract from its usefulness on a larger preparative scale.

In response to the need for preparative electrophoretic separations, apparatus have been developed which separate solutes contained within a continuous liquid flow. For example, British Patents Nos. 1,150,722 and 1,186,184 to Philpot describe an annular elecrophoresis chamber through which solutes and solvent flow. An electric field is applied radially, i.e., perpendicular to the solvent flow, causing solute molecules to migrate as concentric rings within the annular chamber. Multiple outlet or collection ports are used to collect the materials flowing out of the chamber in different fractions taken at varying radial distances from the center of the annulus.

Another apparatus for continuous flow electrophoresis utilizes laminar flow of solvent and solutes through a very thin rectangular chamber. Hannig, K., *Electrophoresis* 3, 235-243 (1982). The electric field causes lateral migration of solutes, and the separated materials are collected through multiple outlet ports at the bottom of the apparatus.

Continuous flow electrophoresis devices of these types have not, however, proven to be suitable candidates for scale-up from a bench-top level. This unsuitability is largely the result of two effects: buoyancy instability as an indirect result of Joule heating creating density inversions within the solvent, and decreased resolution due to convective and electroosmotic dispersion of solute molecules. These difficulties become more pronounced as the electrophoretic apparatus becomes larger and the residence time of ions in the field becomes longer—changes which are associated with preparative separations and those involving difficult-to-separate solutes.

A related technique, isoelectric focusing, can also be used to achieve separation of solutes, particularly of biological molecules. In isoelectric focusing, a pH gradient is imposed upon the solute between the electrodes. A solute molecule migrates in the field until it reaches the point in the pH gradient where it is electrically neutral. This type of separation can also be carried out in a continuous flow apparatus, and may be improved by recycling the flow through the chamber. U.S. Pat. Nos. 4,204,929 and 4,362,612 to Bier describe apparatus for recycle isoelectric focusing (RIEF).

It should be understood, however, that electrophoresis and isoelectric focusing are fundamentally distinct techniques. Electrophoretic separations are rate-driven separation processes in which solute migration continues as long as the electric field is applied. In contrast, isoelectric focusing is an equilibration-process in which solutes only migrate until they reach their characteristic equilibrium point within the pH gradient. For this reason, improvements which are effective for one type of separation technique would not be theoretically expected to improve the other type of technique.

BRIEF DESCRIPTION OF THE INVENTION

According to the present invention, electrophoretic separations with improved resolution can be obtained using recycle continuous-flow electrophoresis (RCFE). RCFE separations can be carried out in a continuous flow electrophoresis chamber having a plurality of inlet ports and a plurality of outlet ports disposed opposite the inlet ports. A sample, which comprises the solutes to be separated and a solvent, is introduced through one or more inlet ports, through the electric field in the chamber, and exits from the chamber via the outlet ports. During exposure to the field, solutes migrate laterally relative to the flow depending on their electrophoretic mobility.

The sample flowing out of each outlet port is recycled back, and reenters the chamber through an inlet port. The recycle stream does not, however, flow from an outlet port to the inlet port directly opposite the outlet, but rather is shifted to reenter the chamber through an inlet port which is displaced from the inlet port directly opposite the outlet port by a predetermined distance $\Delta$ in the direction opposite to the migration of the higher mobility solute. The distance $\Delta$ is given approximately, to within 10% in most practical applications, by the equation $$\Delta \cong \frac{L}{2} \left\{ \frac{(\mu_1 + \mu_2) E}{V_{av}} \right\}$$

where L is the electrode length, $\mu_1$ and $\mu_2$ are the electrophoretic mobilities of the solutes, E is the electric field strength, and $V_{av}$ is the average velocity of the sample flow.

An RCFE apparatus may also include regenerator sections located on each side of and contiguous with the separation chamber. The regenerator sections act to accumulate and concentrate the separated materials on opposite edges of the chamber. In the regenerator sections, the flow from the outlet ports is directed to inlet ports displaced either one or more port widths more, in the case of the regenerator toward which the higher mobility solute migrates, or one or more port widths less than the distance which the flow in the separation section is displaced. Since the finite size of the ports effectively quantizes the shifts, the shifts in the regenerator sections can be said to be one or more ports larger, or smaller, than the shifts in the separation section.

DETAILED DESCRIPTION OF A PREFERRED EMBODIMENT

Figure 2:
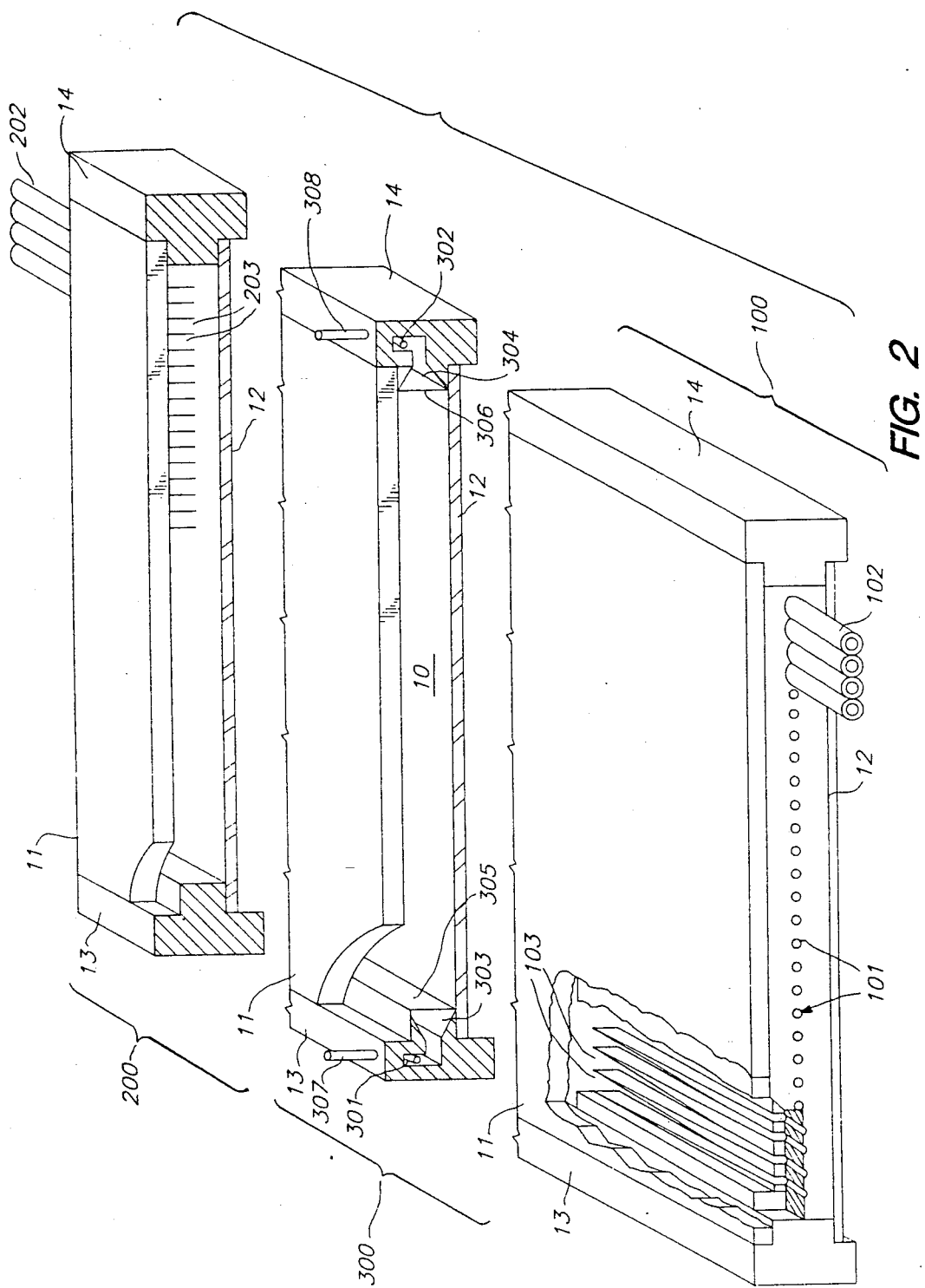
FIG. 2 is a schematic diagram in broken perspective of an RCFE apparatus employed in the system shown in FIG. 1.

Referring first to FIG. 2, an RCFE apparatus according to the invention may comprise a slit like separation chamber 10 formed by closely spaced parallel plates 11 and 12 and side wings 13 and 14. The plate 11 should be made of an adiabatic material so that it neither gives up nor receives heat from its surroundings. Plate 12 should be made of a material with high thermal conductivity since, in operation, plate 12 is contacted with a heat exchanger (not shown) to provide temperature control of the fluid in the separation chamber. Suitable materials for plate 11 include plastics or glass, while plate 12 can be advantageously made of a metal sheet, e.g., aluminum or stainless steel, coated with an inert material such as polytetrafluoroethylene.

At one end of the separation chamber 10 is located an inlet port section 100 which is formed from extensions of parallel plates 11 and 12 and side wings 13 and 14. The inlet port section 100 contains a plurality of inlet ports 101 which are adapted for attaching tubing 102 thereto. In order to minimize dispersion at the transition from the inlet port section 100 to the separation chamber 10, preferably each inlet port 101 communicates with the separation chamber through a diverging trough 103 which is wider on the end towards the separation chamber 10. Desirably, each of the troughs 103 should be open at the bottom so that the fluid passing therethrough will be in communication with the lower plate 12 for heat exchange therethrough to facilitate temperature control of the fluid in the separation chamber. In the interest of clarity, the troughs 103 are shown in FIG. 2 with the upper walls removed. It will be understood, however, that they are open only on the bottom.

At the opposite end of the separation chamber 10 is located an outlet portion section 200 which is formed from extensions of parallel plates 11 and 12 and side wings 13 and 14. The outlet port section 200 is essentially the reverse of the inlet portion section 100, so that fluid from the chamber 10 passes through a plurality of troughs 203 which converge toward a plurality of outlet ports from which the fluid is discharged through tubing 202.

In the separation section 300, the side wings 13 and 14 each have an electrode extending for the length of the separation chamber 10. In a simple embodiment, the electrodes are merely metal plates, preferably platinum, attached to the side wings 13 and 14 so as to contact the fluid in the separation chamber 10. In a preferred embodiment as depicted in FIG. 2, the electrodes 301 and 302 are disposed within electrolyte chambers 303 and 304 which are isolated from the separation chamber 10 by membranes 305 and 306. The membranes 305 and 306 allow electrical contact between the fluid in the separation chamber 10 and an electrolyte in the electrolyte chambers 303 and 304, but do not allow convection of ions between the chambers. The electrodes 301 and 302 are connected to posts 307 and 308 for connection to a constant voltage power supply 25 (FIG. 1) to generate an electric field within the separation chamber 10 in the known manner.

The chamber 10 can be constructed in essentially any size, according to the throughput required. The thickness of the separation chamber 10, i.e. the distance between plates 11 and 12, should be between 0.1 cm and 1 cm in order to maintain adequate flow continuity and to allow for adequate cooling. For thicker chambers, the electric field strength should be reduced in order to avoid buoyancy-induced unstable convection. The length of the separation chamber 10 should be between 10 cm and 100 cm to obtain good resolution of the solutes to be separated.

The inlet and outlet ports should be of equal number and size, and be equally distributed along the ends of the apparatus. The ports can be of any shape, e.g. rectangular or round, as long as flow turbulence is not introduced by the ports. Turbulence is preferably controlled by the use of diverging troughs 103 adjacent to each port, as shown in FIG. 2.

In a practical RCFE apparatus according to the invention, the inlet and outlet ports can be up to 10 cm$^2$ in size, although smaller ports are preferred. The use of a larger number of smaller ports allows for greater variability of voltage applied to the electrodes 301 and 302, since the available quantized values of $\Delta$ are more numerous and closer together. The lower limit of acceptable port size is defined solely by the need to provide tubing attachments. Preferred ports are from 0.01 cm$^2$ to 1 cm$^2$ in size.

Figure 1:
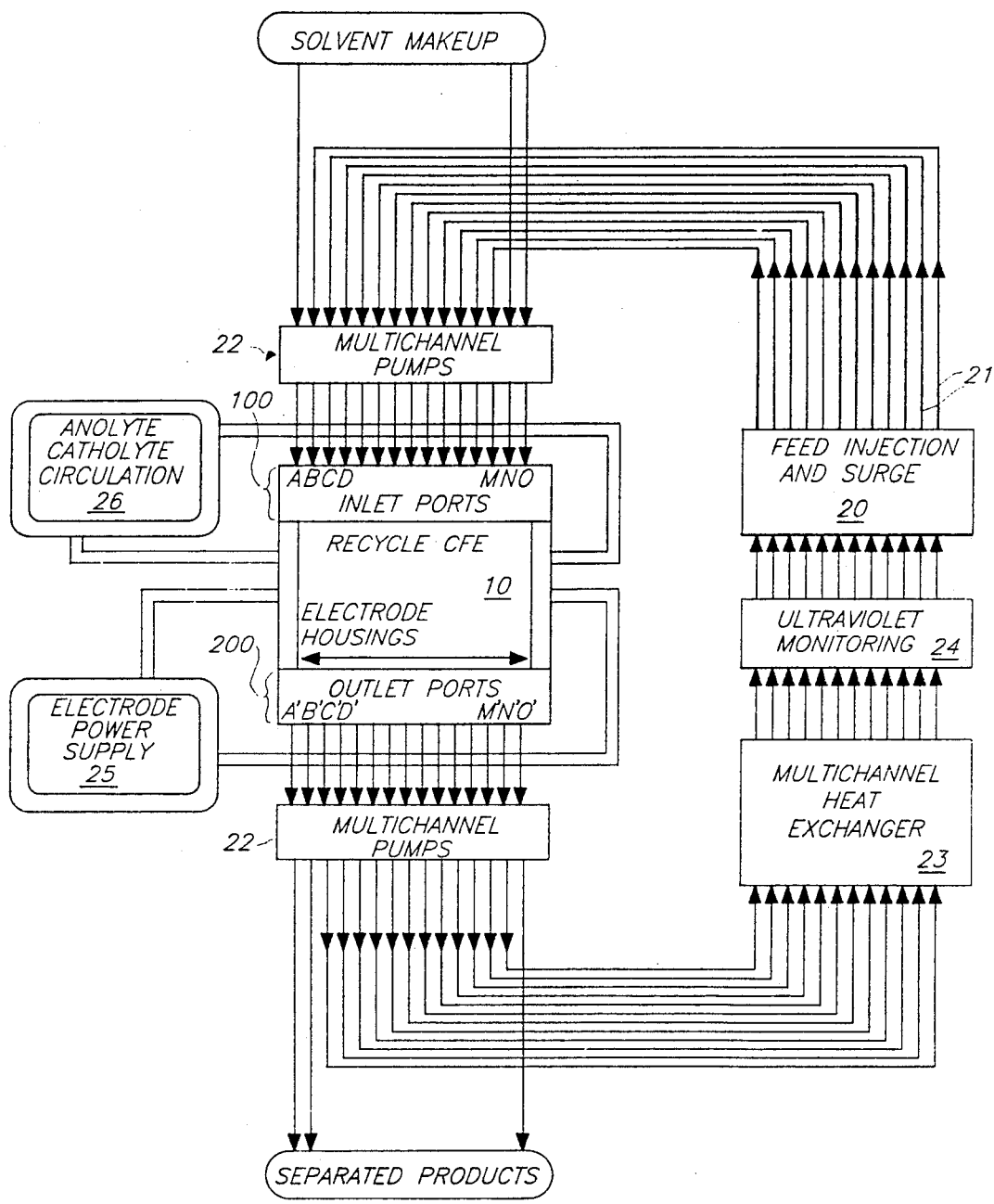
FIG. 1 is a schematic representation of an RCFE separation system according to the invention.

As shown in FIG. 1, flow is introduced through the inlet port section 100, passes through separation chamber 10, and exits through the outlet port section 200. The feed containing the solutes to be separated is introduced into the solvent flow by a conventional feed injection and surge control device 20 which serves to prevent increases or decreases in solvent flow due to the introduction of the solute stream. The solutes are added to one or more of the feed lines 21 prior to introduction of the flow to the inlet ports.

Fresh solvent is supplied through inlet ports A, N, and 0. Solvent and one of the separated solutes are recovered through outlet ports A' and B'. Solvent and the other separated solute are recovered through outlet port O'.

According to the invention, flow from the remaining outlet ports is recycled to the inlet ports for additional passes through the electric field. The recycle flow is not supplied to the inlet port directly opposite an outlet port, however, but is shifted by an amount $\Delta$ which depends on the solutes and the apparatus. By way of example, for a system which requires a shift $\Delta$ equal to the width of one port, the flow from the outlet port C' is recycled to the inlet port B, D' is recycled to C, and so on up to N' to M. The recycle section of the chamber may comprise any desired number of ports. As a practical matter, 20 to 40 pairs of ports (0.1 cm$^2$ to 1 cm$^2$ in size) are entirely adequate for the effective separation of solutes whose electrophoretic mobilities differ by 10% to 20%. Solutes whose mobilities differ by more than 20% can be separated by using fewer ports in the recycle section.

As best shown in FIG. 1, the RCFE apparatus may be located within a loop of conduits for recycling the flow from the outlet ports. A multi-channel pumping means 22 is used to propel the fluid flow through the separation chamber 10 and around the recycle loop. Preferably, pumps are provided both before and after the separation chamber. Optionally, a heat exchanger 23 can be provided to control the temperature of the recycled flow, and a conventional ultraviolet detector 24 can be provided to detect solutes. Also, conventional means 26 is provided for circulating anolyte and catholyte through the electrolyte chambers 303 and 304.

RCFE increases the resolution of an electrophoretic separation by increasing the effective length of the chamber. A lateral, i.e., cross-flow, shift of the recycle flow eliminates dispersion of the solute which would normally reduce resolution in a chamber of increased length. The critical factor to achieving this solute rectification is the magnitude of the lateral shift, i.e. how many ports the recycle flow is displaced. No separation is achieved if the shift is too small, and a shift which is too large actually leads to increased dispersion.

The determination of the proper shift distance, $\Delta$, for any pair of solutes requires the consideration of many factors. These factors include physical attributes of the electrophoretic chamber, such as the length, breadth and thickness of the chamber and of the regenerators; and properties of the solutes themselves, such as the electrophoretic mobilities of the solutes as well as the properties of the carrier electrolyte. The strength of the electric field, the electroosmotic velocity, and the flow rate of the solvent also need to be considered.

According to the invention, the proper shift, $\Delta$, is given to within 10% defined for a given pair of solutes by the equation $$\Delta \simeq \frac{L}{2} \left( \frac{(\mu_1 + \mu_2) E}{V_{av}} \right)$$

where L is the length of the chamber (cm), $\mu_1$ and $\mu_2$ are the electrophoretic mobilities of the solutes ($\mu$m/sec-cm/volt); E is the electric field strength (V/cm); $V_{av}$ is the average velocity of the sample flow through the chamber (cm/sec). This equation is approximately correct for separation chambers of arbitrary thickness, and for separation conditions under which solute dispersion is not extreme. Such conditions will exist when the lateral width of the chamber recycle section is sufficiently broad so that it passes the highly dispersed solute entrained near the transverse walls through the chamber several times.

Figure 3A:
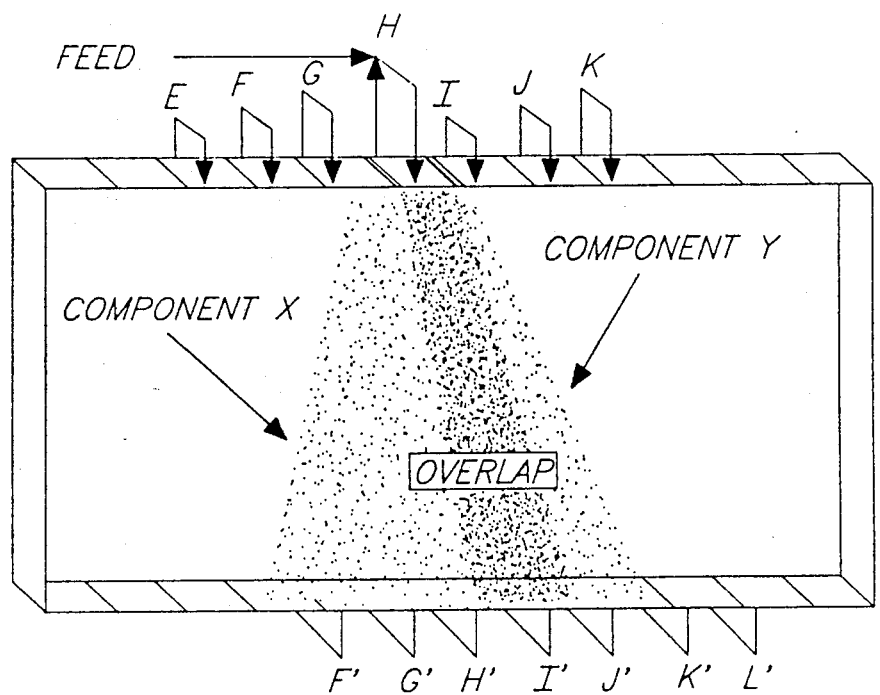
FIGS. 3a and 3b show sequential distribution patterns for a discrete group of instantaneously introduced solute molecules to illustrate how separation occurs in an apparatus according to the invention.
Figure 3B:
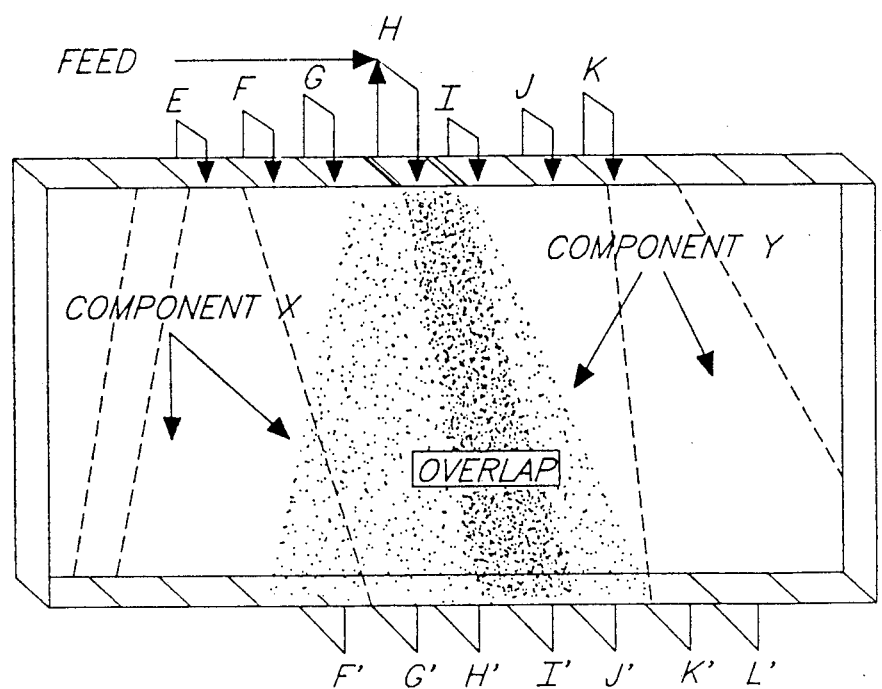

For a better understanding of the invention, reference is made to FIGS. 3a and 3b which illustrate the passage of a discrete group of instantaneously introduced solute molecules through the separation process. Only a few central ports from the recycle section of an RCFE apparatus such as that in FIG. 1 are shown.

FIG. 3a shows an initial pass through the separation apparatus. A mixture of component X and component Y are introduced through inlet port H. If no electric field were applied, the mixture would spread out in the solution fairly uniformly as it flowed through the chamber, resulting in a distribution of the solute mixture resembling a narrow conical section. When an electric field is applied, however, one of the solutes will migrate more rapidly, so that there will be in fact two different conical distribution patterns, skewed to differing extents in the direction of migration.

In FIG. 3a, the distribution of component X, the slower migrant, is shown as an essentially unskewed conical section, while the distribution of component Y has been skewed toward the right-hand side of the figure by the electric field. In the center, the two distributions overlap at this stage of the separation. It can be seen that toward the left of the chamber there is a region containing essentially pure component X and that a region of essentially pure component Y exists on the right. At this point, the solute flow reaches the outlet ports, and is recycled.

The flow which reaches outlet ports F' and G' contains essentially only component X. This flow is recycled to inlet ports E and F. As shown in FIG. 3b (for inlet port E) the recycled flow then spreads out as it passes through the chamber. It is clear that as a result of the recycle, the purified component X has been moved further to the left, and will continue to be moved left with each subsequent recycle.

The flow which reaches outlet port I', and to a lesser extent that reaching outlet port H', contains both components X and Y. The flow from outlet port I' is recycled and reintroduced through inlet port H. As in the first pass through the chamber, this material spreads out and is separated, again forming an essentially conical distribution with component X on the left, component Y on the right, and a region of overlap in the center.

The flow which reaches the outlet ports K' and L' contains essentially purified component Y'. For illustrative purposes, FIG. 3b shows the solute distribution pattern which results when the flow from the outlet port L' is recycled to the inlet port K'. The same skewed conical distribution results for component Y in FIG. 3a, but since the starting point is further to the right, i.e., inlet port K rather than inlet port H, purified component Y is effectively shifted toward the right-hand edge of the chamber.

In a continuous separation, of course, solute molecules are not introduced instantaneously, and the patterns shown in FIGS. 3a and 3b would not be actually observable. Whether the solutes to be separated, however, are introduced as a pulse through the feed line or in a continuous fashion, the molecules will separate in the manner predicted by this model.

A preferred embodiment of the present invention incorporates regenerator sections at each end of the separation chamber to accumulate and concentrate the solutes as they are separated. Each regenerator section comprises a chamber portion which is contiguous with the separation chamber of the basic apparatus, and a plurality of inlet and outlet ports arranged in opposing positions as in the basic apparatus. In the regenerator sections, however, the recycle of flow from the outlet ports is shifted either one or more ports further or one or more ports less than the recycle flow in the separation chamber. For example, in FIG. 4, a regenerator section 41 consisting of four-unshifted recycle loops is shown on the left hand side, the side where the low mobility solute collects. This leaves an outlet port E' which is not involved in the recycle flow through which the low-mobility solute is removed. According to the present invention, the regenerator section for the low mobility solute should be shifted by one or more ports less than the shift in the recycle section.

Figure 4:
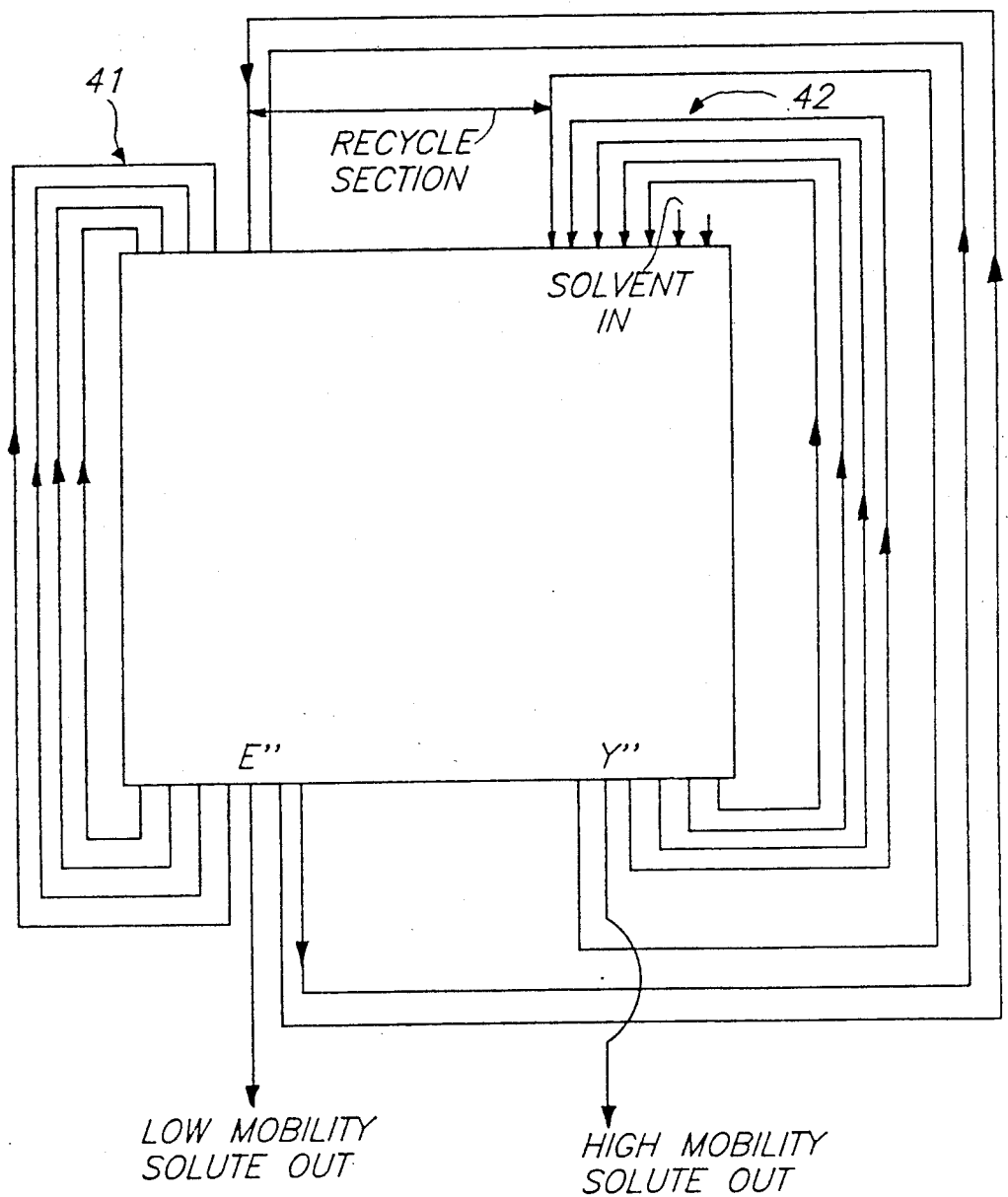
FIG. 4 is a schematic representation showing the path of solvent flow for an RCFE separation apparatus with regenerator sections according to the invention.

On the right hand side of FIG. 4, there is shown a four recycle loop regenerator section 42 for the high mobility solute. Regenerator sections for the high mobility solutes should be shifted one or more ports farther than in the recycle section. In FIG. 4, the shift is two ports. As on the low mobility side, there is an outlet port V″ between the recycle section and the regenerator section which is not involved in recycle. A stream containing the high mobility solute is recovered through this outlet port V‴. From 5 to 20 pairs of ports can advantageously be used in each of the regenerator sections.

In another embodiment of the RCFE apparatus according to the invention, multiple feed ports are included to increase throughput of the device without significant loss of resolution. In this embodiment, the solute mixture is introduced through more than one of the inlet ports in the recycle section. For example, a device in which twenty-one inlet ports of a thirty-one port recycle section have inlets for solute feed shows only a slight decrease in resolution, yet the throughput and outlet concentrations are increased in direct proportion to the number of feed ports utilized.

RCFE can be effectively used to separate solutes whose electrophoretic mobilities differ by at least 10%. The solutes are dissolved in an electrolyte buffer and passed repeatedly through an RCFE chamber to achieve separation. While essentially any electrolyte solution can be used, preferred electrolytes contain various salts and buffering agents of ionic strength less than 0.01 molal and hydronium ion concentrations such that the pH is between 3 and 9. The technique is particularly suitable for separations of biological molecules in dilute solution since further dilution of the solutes can be minimized.

The following examples will serve to illustrate the operation of the method and apparatus of the invention in the separation of specific pairs of solutes.

EXAMPLE 1

A mixture of 0.2 micron and 0.8 micron diameter polystyrene latex particles is separated under the following conditions:
Electric Field Strength (E): 25 volts/cm
Electrode Length (L): 16 cm
Centerline Fluid Velocity ($V_{max}$): 0.930 cm/sec
Average velocity ($V_{av}=2/3\ V_{max}$) 0.62 cm/sec
Lateral Port Thickness: 0.5 cm
Transverse Port Thickness: 0.5 cm
The electrophoretic mobilities for the two sizes of particles are 6.5 $\mu$m-cm/volt-sec and 9.2 $\mu$m-cm/volt-sec respectively. Calculation of $\Delta$ yields a value of 0.51 cm for the required shift to achieve separation and accordingly a shift of one port width to the left is used.

Under these conditions, essentially complete separation is obtained in an RCFE according to this invention having 61 recycle ports and no regenerator sections. The feed is introduced through the center inlet port (#31). The effluent removed from the left-hand side contains 98.96% of the 0.2 micron particles in the original feed, and none of the 0.8 micron particles. The effluent removed from the right-hand side of the apparatus contains 1.04% of the 0.2 micron particles in the feed and 99.9% of the 0.8 micron particles.

EXAMPLE 2

A mixture of human red blood cells and sheep red blood cells is separated under the following conditions:
Electric Field Strength (E): 25 volts/cm
Electrode Length (L): 16 cm
Centerline Fluid Velocity ($V_{max}$) 0.160 cm/sec
Average velocity ($V_{av}=2/3\ V_{max}$) 0.107 cm/sec
Lateral Port Thickness: 0.5 cm
Transverse Port Thickness: 0.5 cm
The electrophoretic mobilities for the two types of blood cells are 1.16 $\mu$m-cm/volt-sec and 1.44 $\mu$m-cm/volt-sec respectively. Calculation of $\Delta$ yields a value of 0.49 cm for the required shift to achieve separation and accordingly a shift of one port width to the left is used.

Under these conditions, essentially complete separation is obtained in an RCFE according to this invention having 61 recycle ports and no regenerator sections. The feed is introduced through the center inlet port (#31). The effluent removed from the left-hand side contains 99.97% of the human red blood cells in the feed, and none of the sheep red blood cells. The effluent removed from the right-hand side of the apparatus contains 0.03% of the human red blood cells in the feed and 99.9% of the sheep red blood cells.

EXAMPLE 3

A mixture of albumin and hemoglobin (human) is separated under the following conditions:
Electric Field Strength (E): 25 volts/cm
Electrode Length (L): 25 cm
Centerline Fluid Velocity ($V_{max}$) 0.080 cm/sec
Average velocity ($V_{av}=2/3\ V_{max}$) 0.053 cm/sec
Lateral Port Thickness: 0.5 cm
Transverse Port Thickness: 0.5 cm
The electrophoretic mobilities for the two solutes are 0.12 $\mu$m-cm/volt-sec and 0.59 $\mu$m-cm/volt-sec respectively. Calculation of $\Delta$ yields a value of 0.42 cm for the required shift to achieve separation and accordingly a shift of one port width to the left is used.

Under these conditions, essentially complete separation is obtained in an RCFE according to this invention having 61 recycle ports and no regenerator sections. The feed is introduced through the center inlet port (#31). The effluent removed from the left-hand side contains 99.9% of the albumin in the feed, and 0.70% of the hemoglobin in the feed. The effluent removed from the right-hand side of the apparatus contains none of the albumin and 99.3% of the hemoglobin in the feed.

It will be understood that an apparatus according to the present invention can be operated with the flow running vertically, in either an upward or a downward direction. The apparatus could also be operated with the direction of flow being horizontal. This latter orientation can further reduce the buoyancy problems which can result from Joule heating, and allows further scale-up of roughly one order-of-magnitude.

Increased throughput can also be achieved by increasing the width of the separation chamber, i.e. the distance between the electrodes. This method of increasing throughput is best reserved for separation of materials with very similar electrophoretic mobilities, however, since increasing the width increases the residence time of solutes in the apparatus. For difficult to separate solutes, increased width is advantageous since the degree of separation increases exponentially with increasing width.

The invention thus provides novel and highly effective continuous flow electrophoretic separation methods and apparatus capable of providing high throughput separations. By recycling the output of each outlet port and shifting it to reenter the separation chamber through an inlet port which is separated a distance from the inlet port directly opposite, the resolution of the separation is substantially increased while the power requirements are reduced. Moreover, by providing regenerator sections on each side of the separation chamber and multiple feed ports within the recycle section, solute dilution is virtually eliminated.

The several method and apparatus embodiments described above are intended only to be illustrative. It will be understood that modifications in form and detail may be made within the scope of the following claims.

I claim:

1. A method for recycle continuous-flow electrophoresis comprising:
   (a) introducing a solvent and a sample comprising the solvent and two solutes to be separated into a continuous-flow electrophoresis apparatus, said apparatus comprising a slit-like electrophoresis separation chamber through which the sample can flow, formed from a front and a back wall and two end walls, and a pair of electrodes positioned on each end wall of the chamber such that an electric field can be generated which is perpendicular to the direction of the sample flow through the chamber, and said apparatus having one or more sample inlet ports disposed in a linear array between a first edge of said front wall and a corresponding first edge of said back wall and centrally positioned between said end walls, a plurality of solvent make-up ports and positioned adjacent to one or both of said end walls, and a plurality of recycle inlet ports disposed between said sample inlet port and said solvent make-up ports; and said apparatus having a plurality of outlet ports disposed between second edges of said front and back walls opposite to the inlet and make-up ports, one or more of the outlet ports toward each end of the chamber being designated as product recovery ports;
   (b) generating an electric field between the electrodes;
   (c) causing the sample and solvent to flow from the inlet and make-up ports through the electric field to the outlet ports;
   (d) collecting the sample flowing out of each outlet port;
   (e) recycling the collected sample from each outlet port that is not a product recovery port to an inlet port which is separated by a distance $\Delta$ from the inlet port which is disposed directly opposite the outlet port, the distance $\Delta$ being given to within 10% for any pair of solutes by the equation $$\Delta = \frac{L}{2}\left(\frac{(\mu_1 + \mu_2) E}{V_{av}}\right)$$

where L is the separation chamber length, $\mu_1$ and $\mu_2$ are the electrophoretic mobilities of the solutes, E is the electric field strength, and $V_{av}$ is the average velocity of the sample flow, whereby the solutes present in the sample are separated, and accumulate in separate portions of the chamber; and (f) concentrating the separated solutes prior to removal from the chamber by passing the flow through regenerator sections located on each end of the apparatus;
   each of said regenerator sections having a regenerator chamber that is contiguous with the separation chamber and a plurality of inlet and outlet ports arranged in a linear array on opposite edges of said regenerator chamber, said regenerator inlet ports being positioned outward of said recycle inlet ports but inward of said solvent make-up ports, and said regenerator outlet ports being positioned between said product recovery ports and the end walls, and further having means for recycling the sample flow from said regenerator section outlet ports to said regenerator section inlet ports; the shift of the recycle flow in the regenerator section towards which the higher mobility solute migrates being one or more ports larger than the shift of the recycle flow in the separation chamber, and the shift of the recycle flow in the other regenerator section being one or more ports smaller than the shift of the recycle flow in the separation chamber.

2. A method according to claim 1, wherein the solutes have electrophoretic mobilities differing by less than 10%.

3. A method according to claim 1, wherein the recycled flow through the electric field is maintained for a period of one to three hours.

4. An apparatus for recycle continuous-flow electrophoretic separation of two or more solutes comprising;
   (a) a separation chamber through which a sample can flow formed from a front wall, a back wall and two opposing end walls;
   (b) a pair of electrodes positioned on said end walls such that an electric field can be generated which is perpendicular to the direction of sample flow;
   (c) one or more sample inlet ports disposed in a linear array on one edge of the chamber between said front and back walls, said edge being substantially perpendicular to the direction of sample flow, said sample inlet ports being centrally positioned between said end walls;
   (d) a plurality of solvent make-up ports laterally disposed relative to said sample inlet ports and positioned adjacent to one or both of said end walls;
   (e) a plurality of recycle inlet ports disposed between said sample inlet ports and said solvent make-up ports;
   (f) a plurality of outlet ports disposed between second edges of said front and back walls opposite to the inlet and make-up ports, one or more of the outlet ports toward each end of the chamber being designated as product recovery ports;
   (g) means for recycling the flow of sample from each outlet port that is not a product recovery port to an inlet port which is separated by a distance $\Delta$ from the inlet port which is directly opposite to the outlet port, said distance $\Delta$ being variable, and being defined based on the properties of the solutes, and the separation apparatus;
   (h) means for introducing the solutes into the sample inlet pores; and
   (i) regenerator sections, said regenerator sections being located on either end of the separation chamber, and each having a regenerator chamber contiguous with the separation chamber, and having a plurality of inlet and outlet ports arranged in a linear array on opposing edges of the regenerator chamber, said regenerator inlet ports being outwardly positioned of said recycle inlet ports but inwardly of said solvent make-up ports, and said regenerator outlet ports being positioned between the product recovery ports and the end walls;

said regenerator sections further having means for recycling the sample flow from regenerator section outlet ports to regenerator section inlet ports; the shift of the recycle flow in the regenerator section towards which the higher mobility solute migrates being one or more ports larger than the shift of the recycle flow in the separation chamber, and the shift of the recycle flow in the other regenerator section being one or more ports smaller than the shift of the recycle flow in the separation chamber.

* * * * *

UNITED STATES PATENT AND TRADEMARK OFFICE
CERTIFICATE OF CORRECTION

PATENT NO. : 5,071,536

DATED : December 10, 1991

INVENTOR(S) : Cornelius F. Ivory

It is certified that error appears in the above-identified patent and that said Letters Patent is hereby corrected as shown below:

Col. 9, line 35, "and positioned" should read --laterally disposed relative to said sample inlet ports and positioned--.

Signed and Sealed this

Sixth Day of April, 1993

Attest:

STEPHEN G. KUNIN

Attesting Officer

Acting Commissioner of Patents and Trademarks